(12) United States Patent
Peterson

(10) Patent No.: US 9,119,880 B2
(45) Date of Patent: Sep. 1, 2015

(54) METHOD FOR TREATING ACUTE KIDNEY INJURY

(71) Applicant: DRP BIOMEDICAL, INC., Carlsbad, CA (US)

(72) Inventor: Dale R. Peterson, Carlsbad, CA (US)

(73) Assignee: DRP Biomedical, Inc., Carlsbad, CA (US)

(*) Notice: Subject to any disclaimer, the term of this patent is extended or adjusted under 35 U.S.C. 154(b) by 0 days.

(21) Appl. No.: 14/351,118

(22) PCT Filed: Oct. 9, 2012

(86) PCT No.: PCT/US2012/059396
§ 371 (c)(1),
(2) Date: Apr. 10, 2014

(87) PCT Pub. No.: WO2013/055702
PCT Pub. Date: Apr. 18, 2013

(65) Prior Publication Data
US 2014/0303117 A1    Oct. 9, 2014

Related U.S. Application Data

(60) Provisional application No. 61/545,582, filed on Oct. 11, 2011.

(51) Int. Cl.
| | |
|---|---|
| *A61K 45/06* | (2006.01) |
| *A61K 31/728* | (2006.01) |
| *A61K 31/77* | (2006.01) |
| *A61K 31/765* | (2006.01) |
| *A61K 31/785* | (2006.01) |
| *A61K 9/00* | (2006.01) |
| *A61K 31/711* | (2006.01) |

(52) U.S. Cl.
CPC .............. *A61K 45/06* (2013.01); *A61K 9/0019* (2013.01); *A61K 31/711* (2013.01); *A61K 31/728* (2013.01); *A61K 31/765* (2013.01); *A61K 31/77* (2013.01); *A61K 31/785* (2013.01)

(58) Field of Classification Search
None
See application file for complete search history.

(56) References Cited

U.S. PATENT DOCUMENTS

| | | |
|---|---|---|
| 2003/0026855 A1 | 2/2003 | Kameneva et al. |
| 2007/0032451 A1 | 2/2007 | Thacker et al. |
| 2007/0032452 A1 | 2/2007 | Thacker et al. |
| 2011/0189166 A1 | 8/2011 | Boucher et al. |

FOREIGN PATENT DOCUMENTS

WO    2008140499 A2    11/2008

OTHER PUBLICATIONS

Prowle, J. et al "Fluid balance and acute kidney injury" Nature Rev. Nephrol. (2010) vol. 6, pp. 107-115.*
Smyth, D. et al "Drag-reducing polymers . . . " Cardiovasc. Drugs Ther. (1990) vol. 4, pp. 297-300.*
Uchino, S. et al "Acute renal failure in critically ill patients" JAMA (2005) vol. 294, No. 7, pp. 813-818.*
Zhao et al., "Drag-reducing polymers diminish near-wall concentration of platelets in microchannel blood flow" (2010). Biorheology, vol. 47, No. 3-4, p. 193-203; NIH-PA Author Manuscript, p. 1-13; especially p. 2, para 3.
ISR dated Feb. 26, 2013, from corresponding PCT application No. PCT/US2012/059396 filed Oct. 9, 2012.
Brands et al., "New insights into the microvascular mechanisms of drag reducing polymers: Effect of the cell-free layer," *PLOS One* 8(10):e77252 (2013).
Chertow et al., "Acute kidney injury, mortality, length of stay, and costs in hospitalized patients," *J. Am. Soc. Nephrol.* 16:3365-3370 (2005).
Coleman et al., "Effects of a drag-reducing polyelectrolyte of microscopic linear dimension (Separan AP-273) on rat hemodynamics," *Circ. Res.* 61:787-796 (1987).
Cotoia et al. "Drag-Reducing Hyaluronic Acid Increases Survival in Profoundly Hemorrhaged Rats", *Shock* 31(3):258-261 (2009).
Ertepinar et al. "Effects of drag reducing polymer on atherosclerosis", *Biorheology* 27(5):631-644 (1990).
Huang et al., "Recombinant human hyaluronidase PH20 does not stimulate an acute inflammatory response and inhibits lipopolysaccharide-induced neutrophil recruitment in the air pouch model of inflammation," *J. Immunol.* 192:5285-5295 (2014) ePub Apr. 28, 2014.
Kameneva et al. "Effect of Drag-Reducing Polymers on the Structure of the Stagnant Zones and Eddies in Models of Constricted and Branching Blood Vessels", *Translated from Izvestiya Akademii Nauk SSSR, Mekhanika Zhidkosti i Gaza* 6:172-175 (1990).
Kameneva et al. "Blood Soluble drag-reducing polymers prevent lethality from hemorrhagic shock in acute animal experiments", *Biorheology* 41:53-64 (2004).
Lyle et al., "Low molecular weight hyaluronic acid effects on murine macrophage nitric oxide production," J. Biomed. Mater. Res. Part A 94A:893-904 (2010).
Marhefka et al. "Drag reducing polymers improve tissue perfusion via modification of the RBC traffic in microvessels", *Biorheology* 46:281-292 (2009).
Mostardi et al., "The effect of drag reducing agents on stenotic flow disturbances in dogs," *Biorheology* 13:137-141 (1976).
Pacella et al., "A novel hydrodynamic approach to the treatment of coronary artery disease," *Eur. Heart J.* 27:2362-2369 (2006).
Pacella et al. "A novel hydrodynamic method for microvascular flow enhancement", *Biorheology* 46:293-308 (2009).

(Continued)

*Primary Examiner* — Leigh Maier
(74) *Attorney, Agent, or Firm* — Myers Bigel Sibley & Sajovec, P.A.

(57) ABSTRACT

The present invention provides methods for treating acute kidney injury through introduction of one or more drag reducing polymers, oligomers, and/or monomers, as well as compositions that include therapeutic amounts of one or more of these drag reducing polymers, oligomers, and/or monomers. These compositions may also include additional components that enhance at least one of the stability, effectiveness, or administerability of the polymers, oligomers, and/or monomers—such as buffers, anti-oxidants, and enzyme inhibitors.

13 Claims, 2 Drawing Sheets

(56) References Cited

OTHER PUBLICATIONS

Pacella et al. "Drag reducing polymers improve coronary flow reserve through modulation of capillary resistance", Biorheology 46:365-378 (2009).

Pacella et al., "Modulation of pre-capillary arteriolar pressure with drag reducing polymers: A novel method for enhancing microvascular perfusion," *Microcirculation* 19:580-585 (2012).

Polimeni et al. "Hemodynamic Effects of a Poly(Ethylene Oxide) Drag-Reducing Polymer, Polyox WSR N-60K, in the Open-Chest Rat", *J. Cardiovascular Pharmacology* 14:374-380 (1989).

Sakai et al., "I.V. infusion of a drag-reducing polymer extracted from aloe vera prolonged survival time in a rat model of acute myocardial ischaemia," *Br. J. Anaesthesia* 98:23-28 (2007).

Sallisalmi et al., "Plasma hyaluronan and hemorheology in patients with septic shock: A clinical and experimental study," Clin. Hemorheol. Microcirc. Feb. 2013.

Sumpio et al. "The Influence of Perfusate Viscosity, RBC Deformability and Drag on the Function of an Isolated Perfused Rat Kidney", J. Surgical Res. 46:4-8 (1989).

Yaklin "Acute Kidney Injury: An Overview of Pathophysiology and Treatments", *Nephrology Nursing Journal* 38(1):13-18 (2011).

International Application No. PCT/US2012/059396, filed Oct. 9, 2012, international preliminary report on patentability mailed Dec. 3, 2013.

European Application No. 12839457.4, filed Oct. 9, 2012, extended European search report mailed Jun. 2, 2015.

\* cited by examiner

METHOD FOR TREATING ACUTE KIDNEY INJURY

BACKGROUND OF THE INVENTION

Drag-reducing polymers were discovered by B. A. Toms in 1949.[1] They are successfully used to increase the speed and reduce the noise of ships, submarines, and torpedoes; to reduce the pumping costs of liquids; to reduce energy losses in two-phase flow; and to increase the throw of sprinkler systems and firefighting equipment.

Drag-reducing polymers (DRP) are long (MW>$10^6$), soluble, linear polymers, with axial elasticity. Polyethylene oxide (PEO) and polyacrylamide are prototypical examples. Addition of 2 to 100 ppm of these polymers will reduce the pressure drop of fluid flowing in a pipe by up to 70% and decrease the drag on a ship's hull by up to 80%.[2]

The mechanism(s) of action of DRP are still not understood completely. It has become clear that the axial elasticity of the molecules are vital to their function.[3] The molecules appear to act as shock absorbers, damping out turbulent eddies. It has also been shown that DRP inhibit the shedding of laminar boundary layer flow into the turbulent flow near surfaces. At the low concentrations where DRP are typically used, they have no effect on the fluid viscosity. Furthermore, the drag-reducing effects of DRP are seen in turbulent flow, but not in laminar flow.

Since blood flow is laminar throughout the body, scientists were surprised to find measurable effects of DRP when added to blood. Subsequent work indicates that DRP reduce flow disturbances at bifurcations such as branches in capillary networks and reduce the thickness of the cell free layer near vessel walls.[4-6]

Reports of beneficial effects of DRP in animals started appearing during the 1970's. Mostardi, et al. showed that polyacrylamide reduced the frequency of flow separation from the aortic wall below a stenosis by 60%.[7] In 1987, Coleman et al. published that polyacrylamide increased cardiac output more than two-fold and reduced peripheral resistance by half.[8] Two years later, they showed that polyethylene oxide increased aortic blood flow, reduced heart rate, increased ventricular and arterial blood pressure, and reduced peripheral resistance.[9] The next year, Ertepinar, et al. showed that chronic infusion of polyacrylamide into guinea pigs significantly reduced the formation of atherosclerotic plaques.[10]

Marina Kameneva kept interest in DRP alive over the subsequent decades. She began working in the field in Russia during the 1980's and brought her interest to the US during the 1990's. In 2004, she published work showing that a high MW PEO and an extract from aloe vera each protects rats from hemorrhagic shock, while rats receiving low MW PEO or saline showed poor tissue perfusion and 80-85% mortality rates. Two years later, she demonstrated that high MW PEO dramatically increased perfusion in dog hearts following stenosis of the left anterior descending coronary artery.[12] In 2007, she published data showing that the DRP from aloe vera protected rats from a severe AMI, while 50% of the control animals died.[13]

Acute Renal Failure

Acute renal failure (ARF) is the sudden loss of the kidney's ability to filter wastes without losing electrolytes. Most often, ARF (also termed acute kidney injury or AKI) is caused by reduced blood flow to the kidneys (prerenal ARF), though about 20% of the cases are due to infections or toxins affecting the kidneys directly (intrinsic ARF), and about 10% are due to blockages downstream of the kidneys (postrenal obstruction).

The incidence of community acquired ARF is only about 100 cases per million population with a mortality rate of 7%.[14] The published incidence of ARF ranges from 1 to 13% of all hospital admissions ($34 \times 10^6$/year in the US) and 20 to 30% of all ICU admissions ($4.4 \times 10^6$/year in the US).[15] Most cases of ARF are acquired in the hospital as a result of complications from other illnesses or interventions. The most common causes are sepsis, hypovolemia, surgery, imaging contrast agents, chemotherapy drugs, NSAIDS, and some antibiotics.

There has been only one study of the incidence of ARF at the national level. Using the 2001 National Hospital Discharge Survey Liangos, et al, found that 1.9% of all hospital discharges showed a code for ARF, which corresponds to a U.S. incidence of 646,000. The mortality rate was 21.3%. The authors validated the study by examining all the 13,237 patients discharged from St. Elizabeth's (Boston) during 2001. 2.6% of the patients were coded for ARF, but lab values showed that 12% of the patients had experienced ARF. Thus, ARF is coded on only about 20% of occurrences (presumably the most serious cases).[16]

The treatment of ARF is to give fluids to reverse hypovolemia and flush toxins while waiting for the kidneys to recover. In some instances, the patients retain too much water or their electrolyte balance suffers to such an extent that they require dialysis. The most common causes of death in ARF patients are heart failure, sepsis, and respiratory failure. Patients who recover from ARF show increased odds of death and chronic kidney disease over the following 5 and 10 years. Dozens of new treatments and drugs that showed promise in animals have been tested clinically in ARF patients, but none have demonstrated benefits in randomized clinical trials. Some of the treatments tested include diuretics to increase urine flow, dopamine and atrial natriuretic peptide (ANP) to increase blood flow to the kidneys, many cytoprotective agents to preserve tubule epithelial cells such as free radical scavengers, heat shock proteins, hemeoxygenase, xanthine oxidase inhibitors, prostaglandins, and calcium channel blockers and, recently, several growth factors to speed the recovery of the proximal tubules.[15]

No one has recognized that the properties of DRP would make them useful in patients suffering renal failure. Two groups looked at the effects of DRP on kidneys 20 years ago and found they are effective as diuretics. In 1987, Smyth, et al. published that a polyacrylamide DRP in rats increased urine and sodium excretion without altering potassium excretion or creatinine clearance.[17] Three years later, they published results using both a PEO and a polyacrylamide in rats showing that each DRP increased diuresis and natriuresis without altering creatinine clearance or potassium excretion.[18] In 1987, Sumpio, et al. tested polyacrylamide buffer solutions containing 10 and 20% RBC's in perfused kidneys. They found a strong interaction between the effects of hematocrit and the DRP on kidney function. For example, the GFR was reduced by the DRP at 10% Hct but increased at 20% Hct.[19] Presumably, interest waned in DRP as an injectable diuretic with the advent of many orally active diuretics. It is important to note that diuresis is contraindicated in patients experiencing ARF. No other work using DRP in the renal field has been published since.

Thus, I was surprised to find such a dramatic benefit of DRP in the treatment of ARF. ARF has been a serious health problem which has not seen any new, successful treatments since dialysis was introduced in the 1970's. It is unfortunate that no one has thought to study DRP as a treatment for ARF until now.

SUMMARY OF THE INVENTION

I have found that introducing DRP into animals experiencing ARF reduces the symptoms and the mortality rate of ARF. There are several known materials that exhibit drag-reducing properties, but a smaller number that have appropriate chemical properties for use in vivo. One such DRP is DNA which can be infused as a soluble molecule, infused as a preparation of cells which will release the DNA, generated in situ by lysing cells in vivo, or enhanced by inhibiting enzymes that would degrade the DNA. Other promising DRP molecules for treatment of ARF include hyaluronic acid, polyethylene oxide, and polyacrylamide.

One of the attractions of using DRP for ARF is that they can be administered after renal failure has occurred. They act as treatments rather than as just preventatives.

The proper dose can be determined by measuring the flow rate at constant pressure drop as a function of concentration of the DRP in blood. In turbulent flow at constant pressure drop, addition of higher concentrations of DRP will increase the flow rate until viscosity effects reduce the flow rate. Doses of 2 to 50 microgram/mililiter have been effective in vivo. Ideally, the DRP will be formulated as a sterile solution in an appropriate pharmaceutical carrier designed to provide stability during storage and rapid mixing with blood upon infusion into a patient. Alternatively, the DRP could be formulated in a more concentrated form in a pharmaceutical carrier designed to be diluted into saline or similar physiologic buffer before infusion into a patient. Appropriate physiologic buffers include hemofiltration buffers, some dialysis buffers, Ringer's Solution, phosphate, lactate, bicarbonate buffered saline, or normal saline.

The infusion rate should be controlled so that the local concentration in the bloodstream near the infusion point does not exceed the level where viscosity effects of the DRP are manifest. If the maximum concentration is greatly exceeded, then the DRP could cause sludging and obstruction of flow in the vein. The maximum concentration can be determined using the simple flow rate measurements at constant pressure as described above. A simple means to prevent this complication is to package the DRP in a physiologic buffer at a concentration less than that at which viscosity effects become measurable. The DRP solution can then be infused at any convenient rate.

Some DRP molecules are prone to degradation in vivo. Polynucleotides and hyaluronic acid are vulnerable to enzymes in the bloodstream that can rapidly reduce the molecular weight of the DRP molecules. This process may be countered by continual infusion of the DRP or by interfering with or eliminating the enzymes that degrade the molecules. DRP molecules can also be mechanically broken by high shear environments such as during mixing or injection via a fine gauge needle.

PREFERRED EMBODIMENTS OF THE INVENTION

DRP: DNA, RNA, PEO, polyacrylamide, hyaluronic acid, hyaluronate, rhamnogalactogalacturonan, aloe vera extract, polyethyleneimine (with hydrophilic pendant groups), glucosaminoglycans, other polyglycans, polyvinylformamide, polyphosphates, polyvinylamine, polyvinylalcohol, polyvinylpyrrolidone, polyacrylic acid, polyacrylamide, or combinations of the foregoing.

Dose: Determined via flow measurements but often between 0.01 and 1000 µg/ml.

Degradation: DNA, RNA, and hyaluronic acid are degraded by enzymes and by shear. PEO, polyacrylamide, aloe vera extract, and rhamnogalactogalacturonan are mechanically degraded. Their effect can be enhanced/prolonged by: (1) minimizing shear during their handling and infusion; (2) continuous infusion; (3) removing the enzymes from the blood (hemofiltration, apheresis, antibodies); and (4) blocking or inhibiting the enzymes with large bolus of low MW DNA, RNA, or hyaluronic acid, removal of needed cofactors, or addition of specific inhibitors to the enzymes.

Delivery method: intravenous, i.m., infusion, cell lysis.

Indications: (1) patients experiencing an increase of serum creatinine by 1.5× over baseline value; (2) patients experiencing 25% or more decrease in glomerular filtration rate (GFR); (3) patients with urine production of less than 0.5 ml/kg/hr for 6 hours or more; (4) patients experiencing a spike in ARF biomarkers such as Kim-1, IL-18, NGAL; (5) patients with chronic kidney disease undergoing high risk procedures such as cardiac surgery, AAA bypass, valve repair, and imaging procedures requiring contrast agents; (6) patients with high risk factors (as judged via scoring systems such as SHARF, Mehta) undergoing high risk procedures; (7) kidney transplant patients; and (8) patients suffering from severe blood loss, or massive bruising or hemolysis.

EXAMPLE 1

Figure 1:
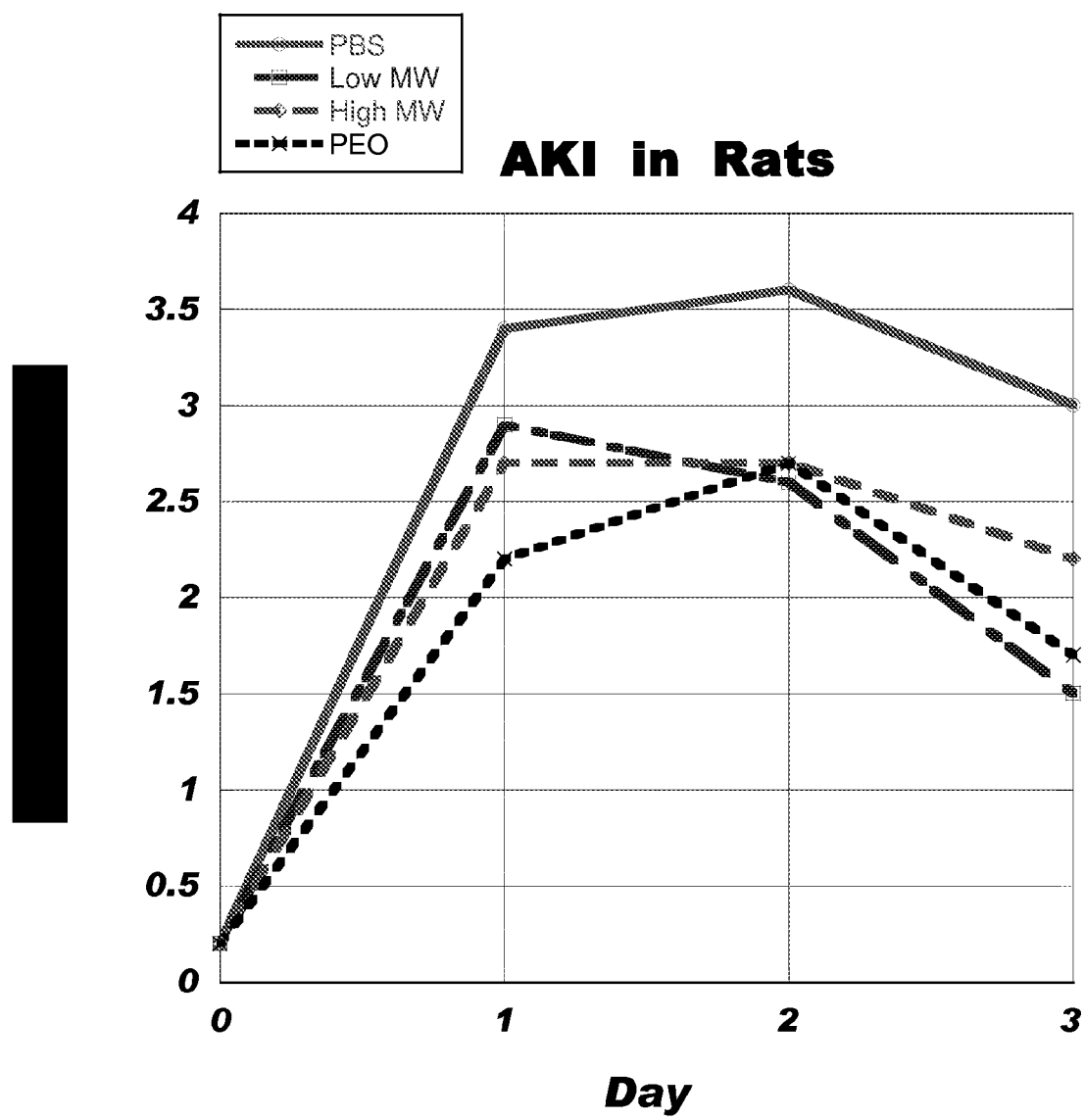
FIG. 1 is a graph of serum creatine over time for each of the test agents.

Preparation of Sterile Solution of High MW PEO

Fifty ml of 50 ppm PEO solution was prepared by weighing 0.0025 gm of $2\times10^6$ Da MW PEO (Sigma, St Louis, Mo.). The PEO was dispersed on the walls of a sterile 50 ml centrifuge tube. 50 ml phosphate buffered saline solution (PBS) was added to the tube and the solution was mixed by rocking the tube. The solution was sterilized using a 0.2 micron pore size syringe filter.

EXAMPLE 2

Preparation of Sterile Solutions of Hyaluronic Acid

Twenty-five ml of 200 ppm hyaluronic acid was prepared by weighing 0.050 gm of hyaluronic acid (1.5×106 Da MW or 6×104 Da MW, LifeCore Biomedical, Chaska, Minn.). The hyaluronic acid powder was dispersed on the walls of sterile 50 ml centrifuge tubes and 25 ml PBS was added to the tubes. The polymers were dissolved and mixed by rocking the tubes. The solutions were sterilized using a 0.2 micron pores size syringe filter.

EXAMPLE 3

Rat Ischemic Kidney Failure Model

Sprague Dawley rats (8-10 wks old, 270 gms) were anesthetized and a blood sample was drawn. The renal artery to the right kidney was occluded for 60 minutes with a clamp and then the kidney was reperfused by removing the clamp. 15 minutes after reperfusion, the left kidney was surgically removed. The incisions were closed with sutures and staples and the animals recovered. 15 minutes after nephrectomy the test agents were slowly infused into the animals via their tail veins. The test agents were phosphate buffered saline (PBS, negative control), high ($1.5 \times 10^6$ Da) molecular weight hyaluronic acid, low ($6 \times 10^4$ Da) molecular weight hyaluronic acid, and high ($2 \times 10^6$ Da) molecular weight PEO. Each test agent was infused into 6 animals, 1.4 ml per animal, for a total of 24 rats in the study. Final blood concentrations of test agents was 3.6 ppm PEO or 14.3 ppm hyaluronic acid.

Blood samples were drawn from each of the animals at 24, 48 and 72 hours post-surgery. All blood samples were used to determine blood urea nitrogen (BUN) and serum creatinine values. The animals receiving hyaluronic acid or PEO showed smaller increases in BUN and serum creatinine from baseline and decreased mortality rates compared to the animals receiving PBS. This is the first data showing the beneficial effects of DRP in ARF.

Right Kidney Ischemia-reperfusion Surgery Procedure: (1) anesthetize the animal; (2) shave the left and right flank regions; (3) apply eye ointment to protect eyes from excessive drying; (4) clean the surgical areas with povidone-iodine solution and 70% ethanol; (5) cut a 2-cm-long incision on right flank, sufficient to expose the right kidney; (6) clamp the artery for 60 minutes; (7) after 60 minutes has passed, remove the clamp; (8) suture or staple edges of skin to close incision; and (9) let the animal recover for 15 minutes then proceed with left kidney removal.

Left Kidney Removal Procedure: (1) cut a 2-cm-long incision on left flank, sufficient to expose the left kidney; (2) place a ligature on kidney artery, vein and the ureter (with 4-0 silk suture), respectively; (3) cut the artery, vein and the ureter on the side of the left kidney and keep the ligatures on the animal; (4) remove the left kidney; (5) suture or staple edges of skin to close incision; and (6) let the animal recover for 15 minutes and then deliver test articles (5 ml/kg) via tail vein.

Blood Collection: Day 0, 1, 2, 3 (96 samples).

Collection and Processing: Collect whole blood (minimum 200 μL of whole blood) from surviving animals on Day 0, 1, 2, 3 (n=24-96 samples). Whole blood will be collected into serum separator tubes, allowed to clot, and then processed into serum and stored on ice or frozen (−80 degrees ° C.) until Clinical Chemistry can be run. 100 μL of serum needed per sample per test.

Clinical Chemistry: Clinical chemistry will be performed using the Critical Care Plus, "The Electrolyte Rotor." Parameters of this rotor include the following: ALT, BUN, CL, CRE, GLU, K+, NA+, $tCO_2$. 24 samples per day for 4 days i.e., 0, 1, 2, 3; or 24-96 total samples depending on survival of the study animals.

Termination: Study termination will occur on Day 3 after Day 3 blood collection for Clinical Chemistry.

The remaining (right) kidney (n<24 kidneys) will be collected in 10% formalin for 24 hours (at room temperature) then transferred to 70% Ethanol and stored at room temperature until delivered to the Client.

End points of the study: Serum for clinical chemistry pre- and post-surgery: Day 0, 1, 2, 3 (4 time points, <96 samples). Kidneys (n<24) will be fixed in 10% formalin and stored in 70% ethanol until clinical chemistry results are available. If the blood chemistry warrants further study, the kidneys will be embedded in paraffin, sectioned, and stained with H&E and periodic acid-Schiff.

Figure 2:
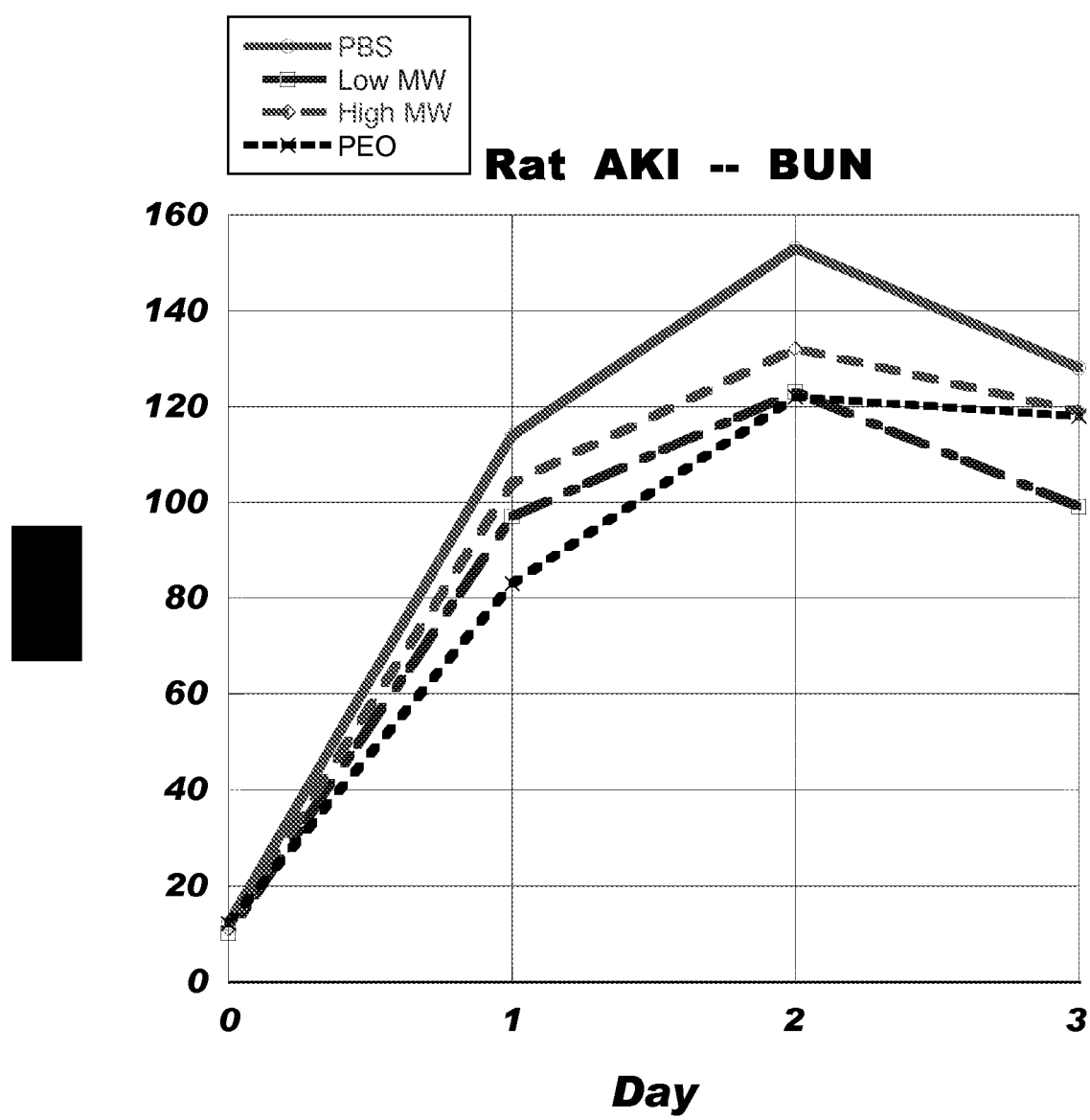
FIG. 2 is a graph of blood urea nitrogen (BUN) over time for each of the test agents.

The results of this experiment are tabulated in Table 1 and plotted in FIG. 1 and FIG. 2.

TABLE 1

Serum Creatinine and BUN values for treatment groups.

| Treatment | Baseline | | Day 1 | | Day 2 | | Day 3 | |
|---|---|---|---|---|---|---|---|---|
| | Mean | Std Dev | Mean | Std Dev | Mean | Std Dev | Mean | Std Dev |
| Serum Creatinine | | | | | | | | |
| PBS | 0.18 | 0.10 | 3.35 | 0.58 | 3.63 | 1.72 | 2.98 | 2.46 |
| Low MW Hyaluronic Acid | 0.17 | 0.10 | 2.87 | 0.39 | 2.58 | 1.35 | 1.52 | 1.08 |
| High MW Hyaluronic Acid | 0.17 | 0.10 | 2.67 | 0.44 | 2.68 | 1.36 | 2.18 | 1.76 |
| High MW PEO | 0.15 | 0.08 | 2.22 | 0.90 | 2.65 | 1.70 | 1.72 | 1.59 |
| BUN | | | | | | | | |
| PBS | 12.0 | 1.4 | 113.7 | 11.1 | 152.8 | 43.4 | 128.4 | 69.1 |
| Low MW Hyaluronic Acid | 10.0 | 1.8 | 97.0 | 11.1 | 123.0 | 43.8 | 98.7 | 52.7 |
| High MW Hyaluronic Acid | 11.2 | 2.0 | 103.5 | 24.6 | 131.8 | 54.0 | 119.2 | 76.7 |
| High MW PEO | 11.5 | 2.2 | 83.0 | 24.2 | 121.5 | 63.3 | 117.8 | 74.5 |

The following publications are incorporated by reference herein in their entirety for all purposes:

1. B A Toms, Proceedings of International Congress on Rheology, Vol. II, pp. 135, North Holland, Amsterdam, 1949.
2. V. T. Truong, "Drag Reduction Technologies", DSTO-GD-0290, Defence Science and Technology Organization, Victoria, Austr., June 2001.
3. H. A. Choi, et al, "Turbulent Drag Reduction and Degradation of DNA", Phys Rev. Lett. 89(8), 088302, 2002.
4. Kameneva M V, Polyakova M S, Fedoseeva E V. "Effect of drag-reducing polymers on the structure of the stagnant zones and eddies in models of constricted and branching blood vessels". Fluid Dyn 25, pp. 956-959, 1990.
5. T. Sakai, et al, "I.V. infusion of a drag-reducing polymer extracted from aloe vera prolonged survival time in a rat model of acute myocardial ischaemia", British Journal of Anaesthesia 98 (1) pp 23-8, 2007.
6. Guyton A C, Hall J E. Overview of the circulation; medical physics of pressure, flow, and resistance. In: Guyton A C, Hall J E eds., *Textbook of Medical Physiology*. Philadelphia, Pa., USA: W.B. Saunders Company; 1996.
7. R A Mostardi, et al, "The Effect of Drag Reducing Agents on Stenotic Flow Disturbances in Dogs" Biorheology, 13, pp 137-141, 1975.
8. Coleman P B, Ottenbreit B T, Polimeni P I, "Effects of a Drag-Reducing Polyelectrolyte of Microscopic Linear Dimension (Separan AP-273) on Rat Hemodynamics" Circ. Res., 61, pp 787-796,1987.

9. Polimeni P I, Ottenbreit B T, "Hemodynamic effects of a poly(ethylene oxide) drag-reducing polymer, Polyox WSR N-60K, in the open-chest rat," J Cardiovasc Pharmacol. 14(3), pp. 374-80, 1989.
10. H. Ertepinar, et al, "Effects of drag reducing polymer on atherosclerosis," Biorheology 27(5), pp 631-644, 1990.
11. M V Kameneva, et al, "Blood soluble drag-reducing polymers prevent lethality from hemorrhagic shock in acute animal experiments," Biorheology 41(1), pp 53-64, 2004.
12. M V Kameneva, et al, "A novel hydrodynamic approach to the treatment of coronary artery disease", Eur Heart J. 27(19), pp. 2362-9 2006.
13. M V Kameneva, et al, "I.V. infusion of a drag-reducing polymer extracted from aloe vera prolonged survival time in a rat model of acute myocardial ischaemia," Br J Anaesth. 98(1) pp. 23-8, 2007.
14. R. Sinert and P. Peacock, "Renal Failure, Acute", eMedicine, http://www.medscape.com/files/emedicine/topic500.htm.
15. B. Molitoris and W. Finn, *Acute Renal Failure*, Philadelphia, W.B. Saunders Co., 2001
16. O Liangos, et al, "Epidemiology and Outcomes of Acute Renal Failure in Hospitalized Patients: a National Survey", Clin J Amer Soc Nephr 1, pp. 43-51, 2006.
17. D D Smyth and P I Polimeni, "Separan AP-273 and renal function: a novel natriuretic substance", Can J Physiol Pharmacol., 65(9), pp 2001-3, 1987.
18. D D Smyth and PI Polimeni, "Drag-reducing Polymers: a Novel Class of Diuretic and Natriuretic Compounds", Cardiovasc. Drugs Ther. 4(1), pp 297-300, 1990.
19. B E Sumpio, et al, "The Influence of Perfusate Viscosity, RBC Deformability, and Drag on the Function of an Isolated, Perfuse sed Kidney", J Surg Res 46, pp 4-8, 1989.

The invention claimed is:

1. A method of treating acute kidney injury, comprising administering to a subject afflicted with said injury drag reducing polymer effective to produce a concentration of said drag reducing polymer in the blood of said subject of between 1 and 100 ppm;
   wherein said drag reducing polymer is polyethylene oxide or polyacrylamide.
2. The method of claim 1, wherein said drag reducing polymer is polyethylene oxide.
3. The method of claim 1, wherein said drag reducing polymer is administered intravenously.
4. A method according to claim 1 wherein at least one component is administered which enhances at least one of the stability, effectiveness or ease of administration of said drag reducing polymer.
5. The method of claim 1, wherein said drag reducing polymer is polyacrylamide.
6. The method of claim 1, wherein said drag reducing polymer is administered to said subject prior to surgery.
7. The method of claim 1, wherein said drag reducing polymer is administered to said subject after surgery.
8. The method of claim 1, wherein said drag reducing polymer is administered to said subject in a repeated dose.
9. The method of claim 8, wherein said drag reducing polymer is administered to said subject at regular intervals.
10. The method of claim 9, wherein said drag reducing polymer is administered to said subject every three days.
11. The method of claim 1, further comprising, prior to administering said drag reducing polymer, determining a target concentration of said drag reducing polymer in the blood based on the severity of the acute kidney injury.
12. The method of claim 1, further comprising, prior to administering said drag reducing polymer, determining a target concentration of said drag reducing polymer in the blood based on a physiologic measurement.
13. The method of claim 12, wherein said physiologic measurement is a creatinine level of said subject.

* * * * *